US010524796B2

(12) United States Patent
Wilson (10) Patent No.: US 10,524,796 B2
(45) Date of Patent: Jan. 7, 2020

(54) APPARATUS FOR IRRIGATING THE VAS DEFERENS (71) Applicant: David S. Wilson, Fort Gibson, OK (US)

(72) Inventor: David S. Wilson, Fort Gibson, OK (US)

(*) Notice: Subject to any disclaimer, the term of this patent is extended or adjusted under 35 U.S.C. 154(b) by 186 days.

(21) Appl. No.: 15/512,821

(22) PCT Filed: Oct. 1, 2015

(86) PCT No.: PCT/US2015/053578
§ 371 (c)(1),
(2) Date: Mar. 20, 2017

(87) PCT Pub. No.: WO2016/057314
PCT Pub. Date: Apr. 14, 2016

(65) Prior Publication Data
US 2017/0290589 A1 Oct. 12, 2017

Related U.S. Application Data (60) Provisional application No. 62/062,059, filed on Oct. 9, 2014.

(51) Int. Cl.
A61B 17/11 (2006.01)
A61F 6/20 (2006.01)
A61B 17/42 (2006.01)

(52) U.S. Cl.
CPC .............. *A61B 17/11* (2013.01); *A61F 6/206* (2013.01); *A61B 2017/1103* (2013.01); *A61B 2017/1125* (2013.01); *A61B 2017/1132* (2013.01); *A61B 2017/4233* (2013.01); *A61B 2217/007* (2013.01)

(58) Field of Classification Search
CPC .... A61M 2025/024; A61M 2025/0177; A61M 2025/0206; A61M 25/02; A61M 2025/028; A61M 2025/0293; A61B 2017/1125; A61B 2017/111; A61B 2017/1132; A61B 2217/007; A61F 6/206
See application file for complete search history.

(56) References Cited

U.S. PATENT DOCUMENTS 3,019,790 A * 2/1962 Militana ............... A61B 17/122
604/116
4,484,911 A * 11/1984 Berlin ................. A61B 17/2812
128/DIG. 26
5,254,095 A * 10/1993 Harvey ................. A61M 5/425
24/563
5,611,794 A 3/1997 Sauer et al.
(Continued)

OTHER PUBLICATIONS

International Search Report and Written Opinion of the International Searching Authority dated Dec. 28, 2015 filed in related application PCT/US15/53578.

Primary Examiner — Nathan R Price
Assistant Examiner — Melissa A Snyder
(74) Attorney, Agent, or Firm — McAfee & Taft (57) ABSTRACT An apparatus for irrigating the vas deferens in connection with a vasectomy reversal is described. The apparatus comprises a fluid delivery device having a first portion that connects to the vas deferens, the fluid delivery device connecting such that a catheter tip inserts into the vas deferens and is held in stable position relative thereto and such that fluid enters the vas deferens through the catheter tip.

4 Claims, 4 Drawing Sheets

(56) References Cited

U.S. PATENT DOCUMENTS

| | | | |
|---|---|---|---|
| 5,704,925 A * | 1/1998 | Otten | A61B 17/00234 |
| | | | 604/115 |
| 5,797,939 A * | 8/1998 | Yoon | A61B 17/122 |
| | | | 606/167 |
| 6,761,725 B1 * | 7/2004 | Grayzel | A61B 17/02 |
| | | | 606/174 |
| 2003/0051735 A1 | 3/2003 | Pavcnik et al. | |
| 2003/0069571 A1 * | 4/2003 | Treat | A61B 18/085 |
| | | | 606/29 |
| 2005/0033353 A1 * | 2/2005 | Jones | A61B 17/282 |
| | | | 606/205 |
| 2007/0078435 A1 | 4/2007 | Stone et al. | |
| 2009/0078270 A1 | 3/2009 | Meier et al. | |
| 2009/0082754 A1 | 3/2009 | Hentrich et al. | |
| 2011/0208022 A1 | 8/2011 | Brawer et al. | |
| 2012/0059215 A1 | 3/2012 | Hong | |
| 2013/0144313 A1 * | 6/2013 | Hahn | A61F 6/204 |
| | | | 606/142 |

\* cited by examiner

APPARATUS FOR IRRIGATING THE VAS DEFERENS

CROSS-REFERENCE TO RELATED APPLICATION

This application claims the benefit of U.S. Provisional Application No. 62/062,059 filed Oct. 9, 2014 and PCT/US/1553578 filed Oct. 1, 2015, both of which are incorporated by reference.

FIELD

This invention relates generally to surgical instruments and, more particularly, to surgical instruments useful in techniques for the anastomosis of the vas deferens, i.e., vasectomy reversal or vasovasostomy.

BACKGROUND

Vasectomies are performed on millions of men worldwide annually. For example, approximately 500,000 vasectomies are performed each year in the United States alone. Of those men that receive vasectomies, approximately five percent of such men subsequently choose to have their vasectomies reversed. Vasectomies generally involve altering the human male anatomy such that sperm cells are unable to mix with seminal fluid.

In a human male, sperm cells are created in the testicles. The sperm cells migrate from the testicles to the epididymis, a long, coiled tube that connects the testicles to the vas deferens. At the time sperm cells enter the epididymis, they are unable to fertilize an egg without assistance. However, the sperm cells mature as they travel through the epididymis and exit the epididymis capable of fertilizing an egg. Mature sperm cells enter the vas deferens from the epididymis and flow through the vas deferens to the seminal vessel. There, the sperm can enter seminal fluid which can then enter a human female and fertilize an egg.

To prevent fertilization, or for any other reason, some men choose to have a vasectomy performed. To perform a vasectomy, a surgeon typically creates an opening in the scrotum using either a scalpel or some other suitable means, and exposes the vas deferens. The vas deferens is then cut or separated and the two resulting open portions of the vas deferens are sealed. For example, each side of the separated vas deferens may be sealed using sutures or cauterization.

The vas deferens is severed to prevent sperm exiting the epididymis from flowing through the vas deferens and ultimately becoming part of the seminal fluid. In this way, any seminal fluid exiting the human male will lack sperm. If seminal fluid does not contain sperm, fertilization cannot take place using traditional means. Therefore, vasectomies can be effective birth control procedures. However, some men wish to reverse a successful vasectomy and restore normal sperm flow.

Generally, two different types of surgeries, or repairs, exist to reverse vasectomies. Whichever surgery is used, the purpose of the surgery is to reestablish the flow of sperm cells from the testicle through the vas deferens. The first repair involves reconnecting the disconnected portions of the vas deferens created by the vasectomy. The second repair is more complicated than the first repair and requires the vas deferens to be reconnected directly to the epididymis instead of the other portion of the vas deferens created by the original vasectomy. Thus, a portion of the vas deferens is bypassed in the second repair.

The first repair is generally preferred because of the differences in size and composition between the vas deferens and the epididymis. The vas deferens is relatively tough and about 3 millimeters in diameter. In contrast, the epididymis is relatively fragile and roughly 0.3 millimeters in diameter. Thus, it is generally easier to surgically reconnect two different portions of the vas deferens than to connect the vas deferens to a portion of the epididymis.

Although the first repair is generally preferred, sometimes the second repair is required. For a variety of reasons, after a vasectomy is performed, obstructions can occur in either the epididymis or the vas deferens. For example, the sperm that are unable to migrate through the vas deferens can form an obstruction, or sperm plug, in either the epididymis or in the portion of the vas deferens still in fluid communication with the testicles. One indication that sperm have formed a speilii plug is the observation that vasal fluid has small clumps of solid material within the fluid.

The second repair, sometimes called epididymal bypass surgery, is much more expensive and complicated than the first repair. The second repair can last about an hour and can require an epidural or a general anesthetic. In contrast, the first repair can require only a local anesthetic and lasts a significantly shorter amount of time.

In addition to the greater complexity of the procedure, the second repair is generally less successful than the first repair. Published studies since the 1980's report sperm return in only 60% to 68% of patients and pregnancy rates in about 25% to 57% of patients. Both ranges are lower than the rates for the first repair. Therefore, if a nonsurgical solution could be found for those patients that had in the past required the second repair, patients could be saved the pain, expense and potential complications associated with the second repair.

BRIEF SUMMARY

In part, the present application relates to an apparatus for irrigating the vas deferens of a patient in connection with a vasectomy reversal. The apparatus comprises a fluid delivery device having a first portion that connects to the vas deferens. The fluid delivery device connects such that a catheter tip inserts into the vas deferens and is held in stable position relative thereto and such that fluid enters the vas deferens through the catheter tip. In some instances, the apparatus can have a fluid delivery device having a first portion that attaches to the adventitia or surrounding connective tissue of the vas deferens.

In some embodiments, the fluid delivery device comprises a catheter assembly, a clamp and a stabilizing bar. The catheter assembly has a first end suitable for connection to a fluid reservoir and terminates at a second end in the catheter tip, which is configured for insertion into the vas deferens. The clamp is configured to clasp around the vas deferens when the catheter tip is positioned within the vas deferens. The clamp and the catheter tip form part of the first portion of the fluid delivery system. The stabilizing bar is connected to the clamp and the catheter assembly such that the clamp and the catheter assembly are held in stable position relative to each other.

In certain embodiments, the clamp has a first interactive tip and a second interactive tip. The first interactive tip and the second interactive tip are shaped to clasp around the vas deferens when the catheter tip is positioned within the vas deferens. The first interactive tip and the second interactive tip can interact to secure the catheter tip in the vas deferens during introduction of a fluid from the catheter to the vas deferens. Further, the first interactive tip and the second interactive tip can interact to secure the catheter tip in the vas deferens during breaking up of an obstruction in the vas deferens by the introduction of the fluid. Additionally, at least one of the first interactive tip and the second interactive tip can have a hook portion which attaches to the adventitia of the vas deferens when the first interactive tip and the second interactive tip clasp around the vas deferens.

In some embodiments, the clamp further comprises a first arm and a second arm. The first arm can comprise the first interactive tip and the second arm can comprise the second interactive tip. The first arm and the second arm can be connected so that the first interactive tip and the second interactive tip can be pressed towards one another. Additionally, the first arm and the second arm can be connected so as to resiliently bias the first interactive tip and the second interactive tip towards one another.

In certain embodiments, the fluid delivery device further comprises a base supporting the catheter assembly. A first end of the stabilizing bar can be connected to the base and a second end of the stabilizing bar can be connected to the clamp. The base can be a closed-end forceps clamp. The forceps clamp can have a handle end and a clamp end with the first end of the stabilizing bar connected to the clamp end.

In some embodiments, the fluid delivery device further comprises a fluid reservoir. The fluid reservoir is configured to hold and release a fluid to the catheter assembly.

The apparatus can comprise a catheter assembly, itself comprising a catheter tip. The apparatus can further comprise a clamp. The clamp can further comprise a first aim and a second arm wherein the first arm and the second arm each further comprise a first interactive tip and a second interactive tip, respectively. The first and second interactive tips can be shaped so as to be able to clasp around the catheter tip and the vas deferens. Additionally, the apparatus can comprise a stabilization bar. The stabilization bar is connected to the catheter assembly and the clamp to allow the first and second interactive tips of the clamp to close around the catheter tip or the vas deferens.

In another embodiment, the apparatus further includes a fluid reservoir. The fluid reservoir is capable of holding and releasing a fluid to the catheter assembly. The catheter assembly is capable of conveying the fluid into the vas deferens.

In another embodiment, the apparatus described in the present application is adapted for irrigating the vas deferens in connection with a vasectomy reversal. The apparatus comprises a catheter assembly having a first end suitable for connection to a fluid reservoir and terminating at a second end in a catheter tip suitable for insertion into a vas deferens. The apparatus further comprises a clamp having a first interactive tip and a second interactive tip where the tips interact to secure the catheter tip in the vas deferens during breaking up of the obstruction. The apparatus further comprises a stabilizing bar connected to the clamp and the catheter assembly such that the clamp and catheter are held in stable position relative to each other.

DETAILED DESCRIPTION OF AN EMBODIMENT

In the description that follows, like parts are marked throughout the specification and drawings with the same reference numerals, respectively. The drawings are not necessarily to scale and the proportions of certain parts have been exaggerated to better illustrate details and features of the invention. Where components of relatively well-known design are employed, their structure and operation will not be described in detail.

Figure 1:
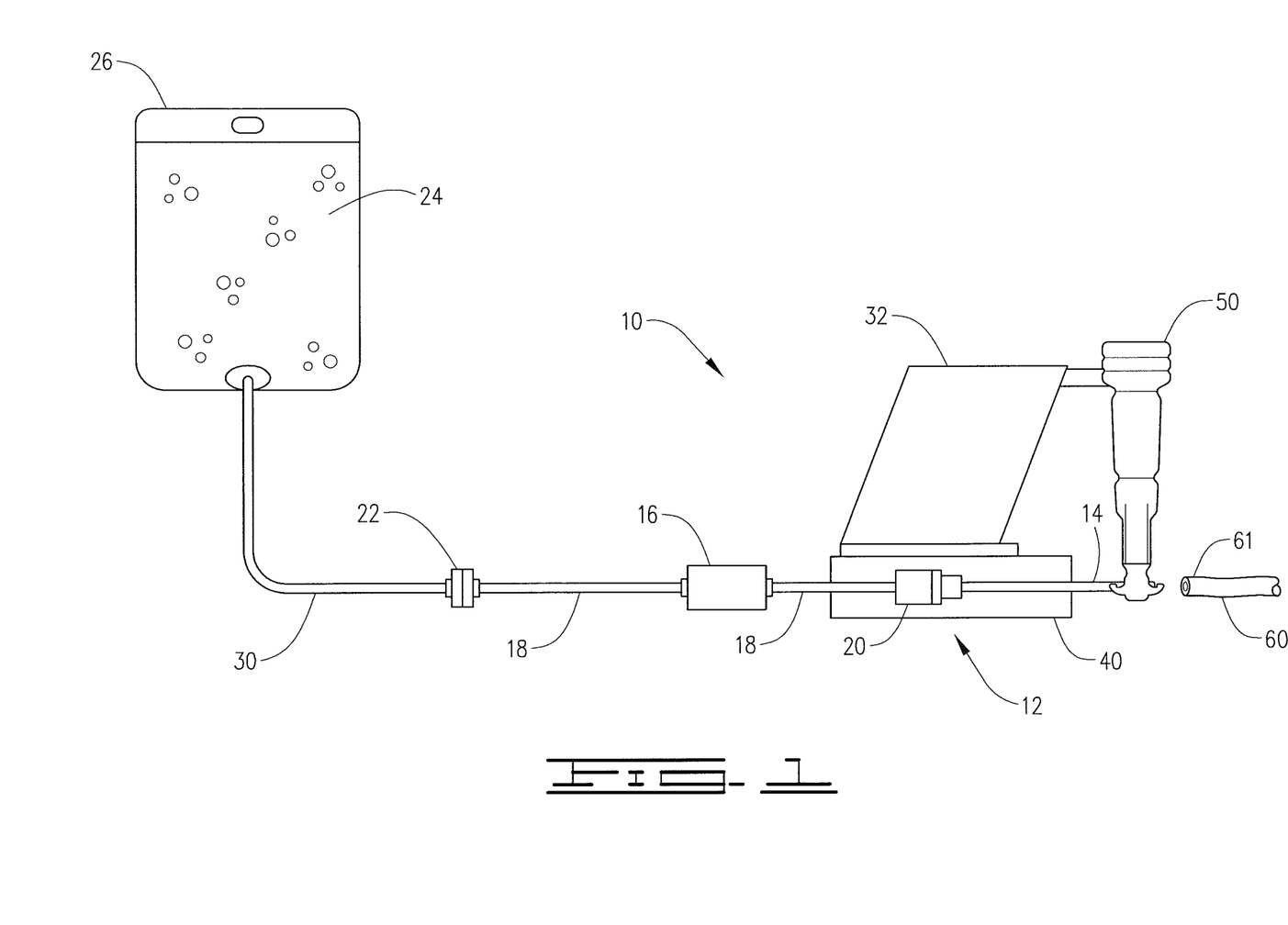
FIG. 1 is a schematic illustration of one embodiment of the apparatus described in the present application.

Referring to FIG. 1, one embodiment of a fluid delivery device or apparatus 10 described in the present application is shown. The apparatus comprises a catheter assembly 12, which is also known as a cannula assembly. Catheter assembly 12 can further comprise several other components. For example, catheter assembly 12 can comprise a catheter tip 14, or cannula tip. Catheter tip 14 is configured so as to be able to enter a vas deferens 20. Catheter tip 14 is further configured so as to be able to deliver a fluid 24 into vas deferens, schematically represented by tube 60.

Catheter tip 14 can optionally be attached to a filter 16. Filter 16 can be positioned such that any fluid flowing through catheter tip 14 is appropriately filtered. In FIG. 1, filter 16 is shown interspaced in fluid transmission line 18.

Generally, catheter assembly 12 will comprise catheter tip 14 and a fluid transmission line 18. In some embodiments, catheter assembly 12 can comprise a single, unitary piece. For example, in some embodiments, catheter assembly 12 can be made of metal. In such an embodiment, catheter assembly 12 can optionally comprise a single metal unit with fluid transmission line 18 and catheter tip 14 being integral so as to form a unitary piece. In other embodiments, catheter tip 14 and fluid transmission line 18 can be two separate pieces joined together. In this case, catheter tip 14 can also be attached to a luer 20. Typically, luer 20 is adapted to provide a leak free connection between catheter tip 14 and fluid transmission line 18. Luer 20 can use any suitable connection method to connect to catheter tip 14. For example, luer 20 can be threaded such that catheter tip 14 can screw into luer 20.

Luer 20 provides a connection between catheter tip 14 and fluid transmission line 18. Fluid transmission line 18 can be connected to luer 20 by any suitable means or can comprise part of luer 20 itself. Fluid transmission line 18 can also be adapted to connect to a fluid line receiver 22, as further described below.

Fluid transmission line 18 can be any material or shape suitable for allowing fluid 24 to flow from a fluid reservoir 26 to catheter assembly 12, through catheter tip 14 and into vas deferens 60. For example, fluid transmission line 18 can be metal or comprise flexible or inflexible plastics or polymers. Fluid transmission line 18 can comprise a single component or can comprise multiple components joined together. For example, the fluid transmission line 18 can be adapted to be detached and reattached to fluid reservoir 26 such that the fluid reservoir 26 can be periodically replaced if desired.

Fluid reservoir 26 is connected to fluid transmission line 18 so as to be in fluid flow communication with catheter tip 14. Fluid 24 flows through catheter assembly 12 and exits through catheter tip 14. Thus, fluid reservoir 26, fluid transmission line 18, catheter assembly 12 and catheter tip 14 can be connected such that fluid 24 can flow into vas deferens 60 and irrigate vas deferens 60 so as to remove obstructions, such as sperm plug.

Figure 2:
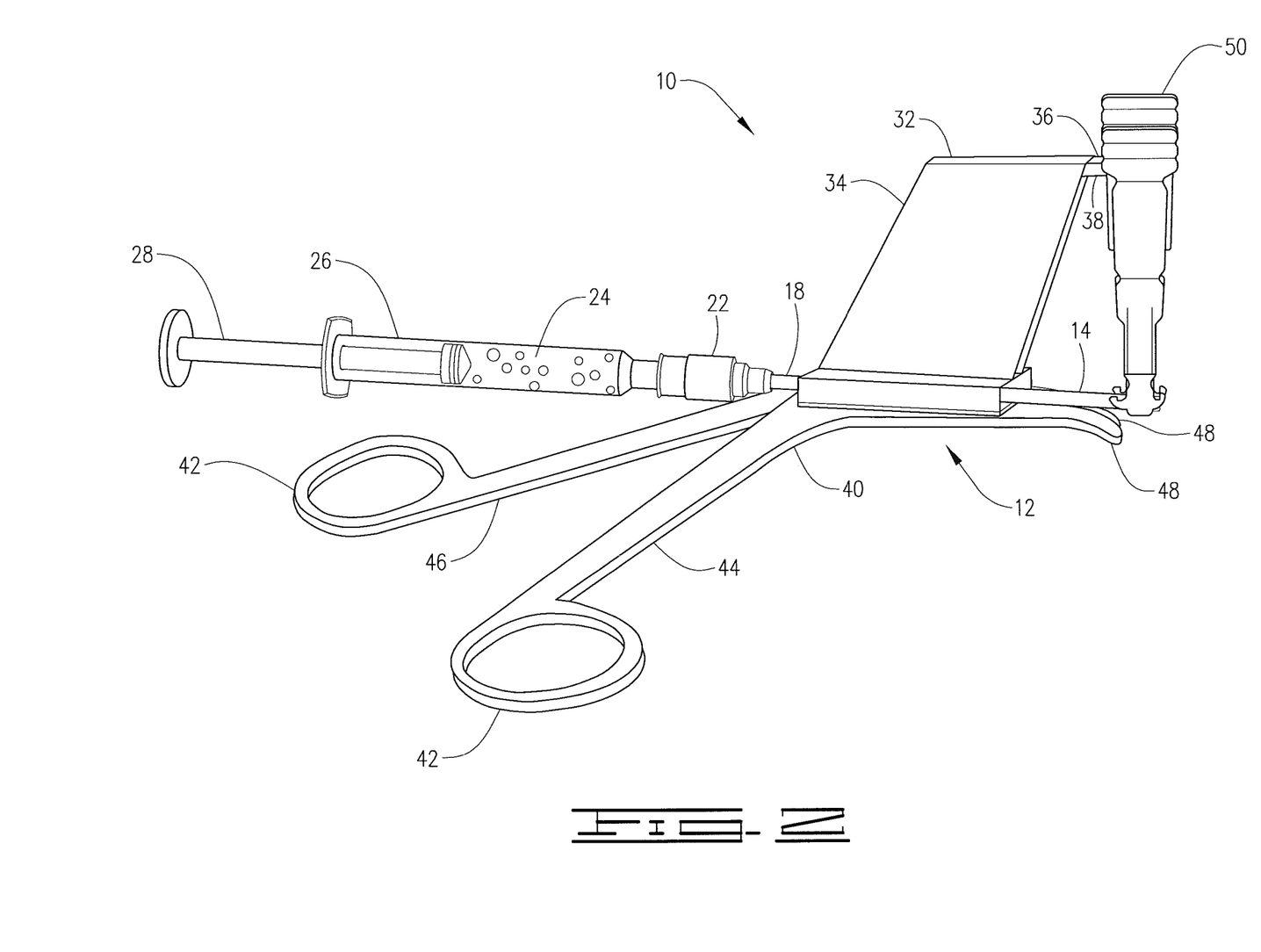
FIG. 2 is a schematic illustration of another embodiment of the apparatus described in the present application.
Figure 3:
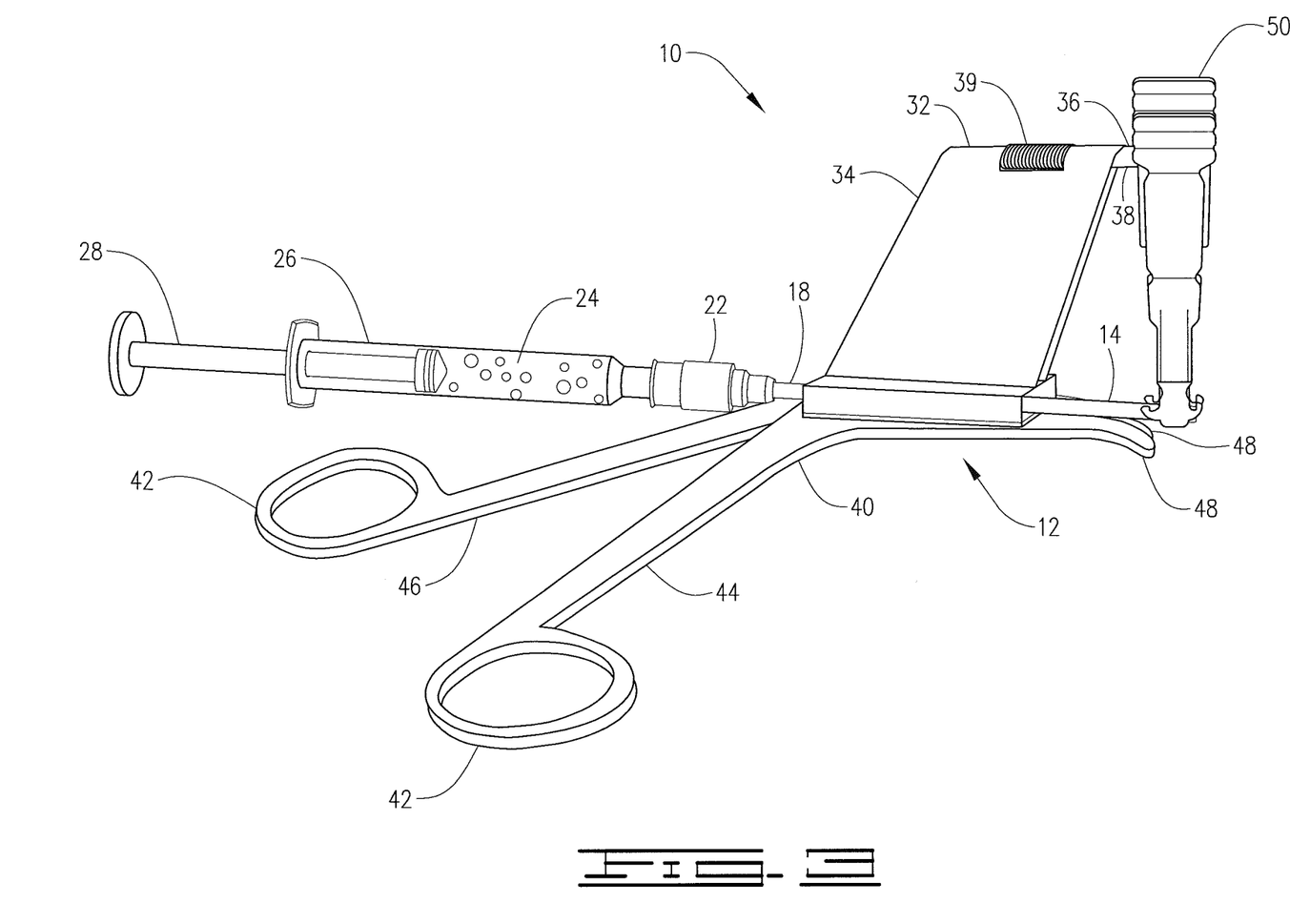
FIG. 3 is a schematic illustration of an embodiment of the apparatus shown in FIG. 2 wherein a rotational connection is used for the stabilization bar.

Fluid reservoir 26 can comprise any suitable material and be of any suitable size. Fluid reservoir 26 can comprise flexible or inflexible plastics or polymers and be sized to contain 5 to 1,000 milliliters. In some embodiments, fluid reservoir 26 can comprise a saline bag, as illustrated in FIG. 1. Typically, the saline bag will be sized to contain 250 to 1,000 milliliters of fluid. In further embodiments, fluid reservoir comprises a syringe as shown in FIGS. 2 and 3. Typically, the syringe will be sized to contain from 5 to 20 milliliters of fluid. For example, fluid reservoir 26 can comprise a syringe sized to hold 10 milliliters of fluid. In such an embodiment, the plunger 28 of the syringe will aid in transmitting fluid 24 from fluid reservoir 26 through fluid transmission line 18, then through catheter tip 14 and into vas deferens 60. As a result, vas deferens 60 is irrigated by fluid 24. Fluid 24 contained in fluid reservoir 26 can be a sterile saline solution.

In some embodiments, fluid transmission line 18 can be directly connected to fluid reservoir 26, such as illustrated in FIG. 2 when a syringe is used as fluid reservoir 26. In other embodiments, typically where a saline bag is used as the fluid reservoir, fluid transmission line 18 can use a second fluid transmission line 30. When second fluid transmission line 30 is used, the two fluid transmission lines 18, 30 are generally connected using fluid line receiver 22. Fluid line receiver 22 functions similarly to luer 20 in that the purpose of fluid line receiver 22 is to provide a leak-free connection between fluid transmission line 18 and second fluid transmission line 30. Second fluid transmission line 30 is connected to fluid reservoir 26, and fluid line receiver 22 can control the flow of fluid 24 from fluid reservoir 26 through second fluid transmission line 30 into fluid transmission line 18 using any suitable means. Fluid transmission line 30 can be connected to fluid line receiver 22 using any suitable means. For example, fluid line receiver 22 can be threaded and second fluid transmission line 30 can be adapted to screw onto or into fluid line receiver 22.

Similarly, second fluid transmission line 30 can connect to fluid reservoir 26 using any suitable means. The connection can include a portion of the fluid reservoir 26. Fluid reservoir 26 is adapted to contain fluid 24 and allow fluid 24 to flow through fluid transmission 18, through any connections, and through catheter tip 14.

Catheter assembly 12 is connected to a clamp 50 using a stabilization bar 32. Stabilization bar 32 is configured to stabilize and position clamp 50 such that claim 50 and catheter assembly 12 are held in stable position relative to each other. The exact position and shape of stabilization bar 32 can vary depending on the exact position and shape of clamp 50. However either is shaped, stabilization bar 32 is positioned or shaped so as to allow clamp 50 to close around catheter tip 14 and vas deferens 60.

In the embodiment illustrated in FIG. 2, stabilization bar 32 is comprised of a first member or mount 34 and a second member or bar 36. Bar 36 is attached to and extends outward from mount 34 such that at a first end (not shown), it is attached to mount 34 and at a second end 38 it is attached to clamp 50 so as to stabilize clamp 50 and hold it in a predetermined position. Bar 36 may be attached to mount 34 by any suitable means which results in bar 36 and clamp 50 being held in a stable position. In some embodiments, bar 36 is attached in an adjustable manner to mount 34. For example, bar 36 can slidingly engage mount 34 such that second end 38 can be extended out from mount 34, as illustrated in FIG. 3. In FIG. 3, the extension of second end 38 is controlled by screw device 39, which interacts with teeth on bar 36 (not shown).

In some embodiments, stabilization bar 32 can be adjustable in shape and orientation. There are a variety of mechanisms that would allow for the adjustment of stabilization bar 32 in shape and orientation. For example, stabilization bar 32 could comprise two members joined by a hinge. In such an embodiment, the hinge would allow the two members comprising stabilization bar 32 to be rotated with respect to one another and thereby adjust the orientation of stabilization bar 32. For a further example, stabilization bar 32 could comprise two or more members rotatably connected to one another. In such an embodiment, the rotation of the members comprising stabilization bar 32 could lengthen or shorten the total length of stabilization bar 32, as illustrated in FIG. 3.

As further illustrated by FIGS. 1, 2 and 3, stabilization bar 32 can be connected to a base 40, which can be part of catheter assembly 12. As illustrated by FIGS. 2 and 3, base 40 can have handles 42 for facilitating positioning of fluid delivery device 10. Base 40 can be of a forceps design as shown. The illustrated forceps design is a closed-end forceps clamp. The forceps base can have first branch 44 and second branch 46 each terminating in a handle 42 at one end and terminating in a tip or clamp end 48 at a second end. Accordingly, the forceps design of base 40 can allow for attachment of the clamp end 48 to the to the tissue surrounding the vas deferens in order to stabilize the apparatus in relation to the vas deferens. Generally, the tissue to which the clamp end 48 is attached will be the vasal sheath or connective tissue immediately surrounding the vas deferens.

As stated, stabilization bar 32 can connect catheter assembly 12 to clamp 50. Clamp 50 can further have any shape suitable to hold catheter tip 14 in place inside vas deferens 60. By stabilizing clamp 50 relative to catheter assembly 12, stabilization bar 32 causes the apparatus to be in a stable position relative to the patient being operated upon.

In some embodiments, stabilization bar 32 or base 40 can have a small chamber or tube (not shown). The chamber or tube is designed to receive catheter tip 14 therein. Thus, catheter tip 14 connects to stabilization bar 32 and base 40 by being introduced into the chamber or tube. In one process using this design, catheter assembly 12 is attached to syringe 26 prior to being introduced into the chamber. Subsequently, catheter tip 14 of catheter assembly 12 is introduced into the chamber so as to place the fluid 24 of syringe 26 in fluid flow communication with the vas deferens.

Figure 4:
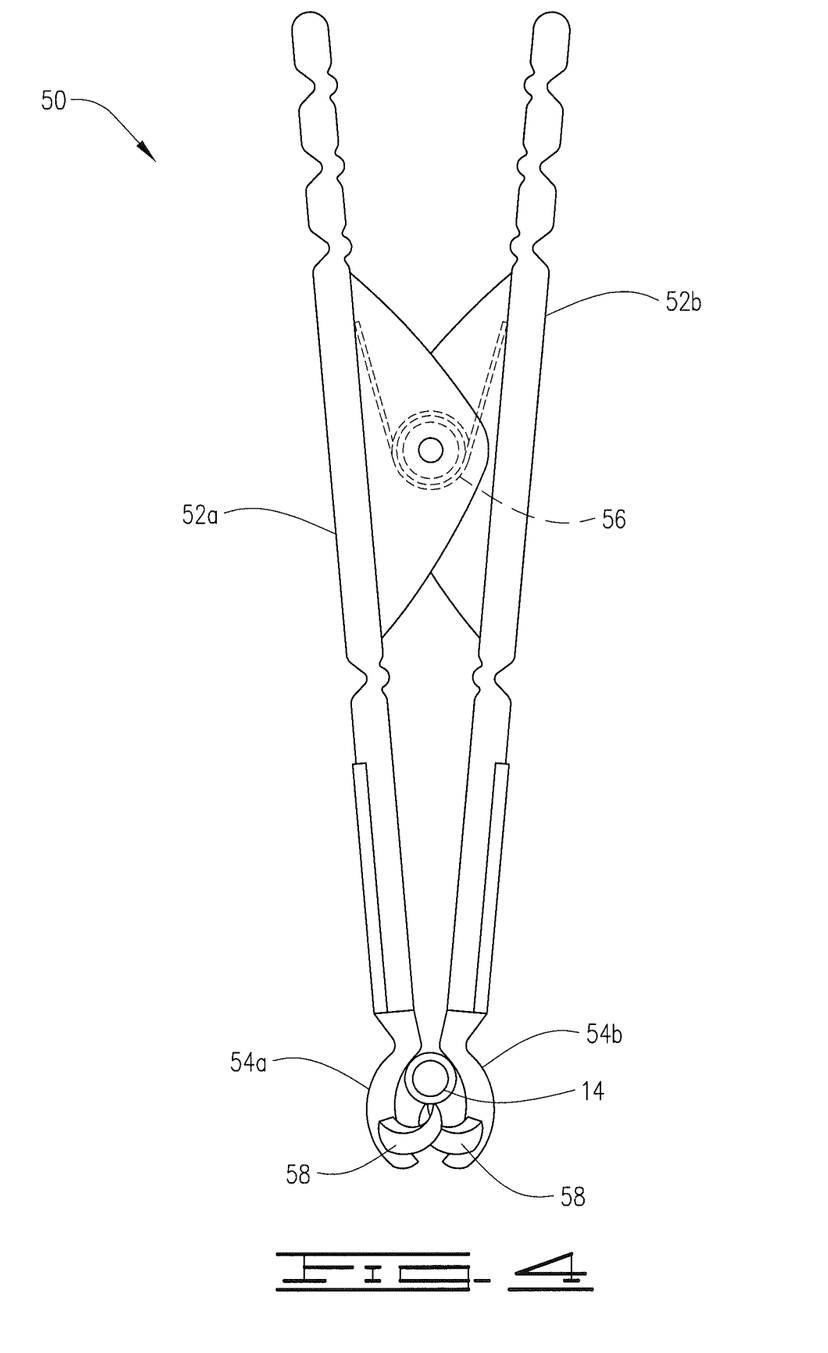
FIG. 4 is a schematic illustration of a frontal view of the clamp portion of an embodiment of the current apparatus.

FIG. 4 provides another view of clamp 50 interacting with catheter tip 14 and vas deferens (not shown). In this view, it is clear that clamp 50 has a first arm 52*a* and a second arm 52*b*. First atm 52*a* and second arm 52*b* can further comprise a first interactive tip 54*a* and a second interactive tip 54*b*, respectively. First interactive tip 54*a* and second interactive tip 54*b* typically comprise the lower portion of first arm 52*a* and second aim 52*b*, respectively. First interactive tip 54*a* and second interactive tip 54*b* are shaped to aid in securing vas deferens 60 around catheter tip 14. In some embodiments, first interactive tip 54*a* and second interactive tip 54*b* can be roughly hemispherical in shape so as to adapt to the cylindrical shape of vas deferens 60 and catheter tip 14. In other embodiments, first interactive tip 54*a* and second interactive tip 54*b* can be nearly straight so as to provide greater pressure on some portions of vas deferens 60 around catheter tip 14.

First interactive tip 54*a* and second interactive tip 54*b* are configured to interact with the particular geometry of catheter tip 14 and vas deferens 60. In the embodiment shown, first interactive tip 54a and second interactive tip 54b are configured to clamp around a cylindrical shape. Because first interactive tip 54a and second interactive tip 54b can have a roughly semi-circular in shape, they are able to clamp around vas deferens 60, hold vas deferens 60 in place around catheter tip 14, and not damage or impart unnecessary force onto vas deferens 60. However, first interactive tip 54a and second interactive tip 54b are not limited to the semi-circular configuration. For example, first interactive tip 54a and second interactive tip 54b may have serrations for strong interaction with vas deferens 60. For further example, first interactive tip 54a and second interactive tip 54b may be triangular in shape such that first interactive 54a and second interactive tip 54b interact with only a portion of vas deferens 60.

In some embodiments, first interactive tip 54a and/or second interactive tip 54b are configured to attach to the adventitia 61 or surrounding connective tissue of vas deferens 60. For example, first interactive tip 54a and second interactive tip 54b can each have hooks 58 which attach each tip 54a, 54b to the adventitia.

First arm 52a and second arm 52b of clamp 50 can press toward one another by any suitable mechanism such that first interactive tip 54a and second interactive tip 54b can clasp catheter tip 14 and vas deferens 60. For example, first arm 52a and second arm 52b can be configured so as to resiliently bias first interactive tip 54a and second interactive tip 54b towards one another. For further example, first arm 52a and second arms 52b of clamp 50 can be pressed toward one another using a spring 56. Other suitable means to press first interactive tip 54a and second interactive tip 54b towards each other may be used, such as a ratcheting connection or screw connection between first arm 52a and second arm 52b.

First arm 52a and second arm 52b can apply sufficient force to vas deferens 60 through first interactive tip 54a and second interactive tip 54b such that vas deferens 60 remains firmly affixed to catheter tip 14. In this way, fluid 24 from fluid reservoir 26 enters vas deferens 60 and does not spill out prior to flushing vas deferens 60. Further, first arm 52a and second arm 52b can apply sufficient force around vas deferens 60 such that a flow of fluid 24 cannot dislodge catheter tip 14 from vas deferens 60.

Clamp 50 can interact with catheter tip 14 and vas deferens 60 with an appropriate predetermined amount of force. For example, if clamp 50 exerts too much pressure on vas deferens 60 and catheter tip 14, clamp 50 could collapse catheter tip 14 and thereby prevent fluid from flowing into vas deferens 60. Additionally, if clamp 50 exerts insufficient pressure on vas deferens 60, fluid 24 may not be forced to flow into vas deferens 60.

In a method using the presently described apparatus, vas deferens 60 must first be exposed. For example, a surgeon can open the scrotum using a scalpel. Any suitable method may be used to expose vas deferens 60 such that a surgeon can interact with vas deferens 60. The surgeon can then make a further incision into vas deferens 60 or otherwise interact with vas deferens 60 in order to open vas deferens 60 to fluid communication with catheter tip 14. If anapparatus in accordance with FIG. 2 or 3 is used, clamp end 48 of the forceps base 40 can be clamped or attached to the vasal sheath or connective tissue immediately surrounding the vas deferens after the tip has been introduced into the incision. Catheter tip 14 can then be inserted into vas deferens 60 in the desired location.

Once catheter 14 is inserted into vas deferens 60, clamp 50 can be attached by placing first interactive tip 54a of first arm 52a and second interactive tip 54b of second arm 52b around vas deferens 60, which also contain catheter tip 14. In this way, clamp 50 can secure vas deferens 60 around catheter tip 14. Next, fluid 24 from fluid reservoir 26 is allowed or caused to flow into vas deferens 60. Fluid 24 flowing from fluid reservoir 26 can flow through fluid transmission line 18 and any connections and into vas deferens 60. The flow of fluid 24 into vas deferens 60 irrigates vas deferens 60. As a result of the irrigation, obstructions in vas deferens 60 can be reduced enough to restore sperm flow through vas deferens 60.

Once obstructions in vas deferens 60 have been removed, the clamp 50 is removed from vas deferens 60 and catheter tip 14 is removed from vas deferens 60. After catheter tip 14 and any obstruction in vas deferens 60 have been removed, the severed portions of vas deferens 60 are reconnected. In this way, sperm flow from the epididymis to the seminal fluid is restored. Once the seminal fluid contains sperm, fertilization of an egg may occur using traditional means.

Although the invention has been described with reference to a specific embodiment, the foregoing description is not intended to be construed in a limiting sense. Various modifications as well as alternative applications will be suggested to persons skilled in the art by the foregoing specification and illustrations. It is therefore contemplated that the appended claims will cover any such modifications, applications or embodiments as followed in the true scope of this invention.

That which is claimed is:

1. An apparatus for irrigating a vas deferens in connection with a vasectomy reversal, comprising:
   a catheter assembly, wherein said catheter assembly comprises a catheter tip suitable for insertion into the vas deferens;
   a vas deferens clamp configured to clasp around the vas deferens when said catheter tip is inserted into the vas deferens;
   a stabilization bar, wherein said stabilization bar is connected to said catheter assembly and said vas deferens clamp so as to hold said vas deferens clamp in position to clasp the vas deferens when said catheter tip is inserted into the vas deferens; and
   a closed-end forceps clamp wherein said stabilization bar is attached to said closed-end forceps clamp and wherein said closed-end forceps clamp is configured to attach to tissue surrounding the vas deferens in order to hold the apparatus in close proximity to the vas deferens when the vas deferens clamp is clasp around the vas deferens.

2. The apparatus of claim 1, wherein said vas deferens clamp further comprises a first arm and a second arm and wherein said first arm further comprises a first interactive tip and said second arm comprises a second interactive tip wherein said first and second interactive tips are shaped to clasp around said catheter tip and the vas deferens.

3. The apparatus of claim 2, further comprising:
   a fluid reservoir, wherein said fluid reservoir is capable of holding and releasing a fluid to said catheter assembly and wherein said catheter assembly is capable of conveying said fluid into the vas deferens.

4. An apparatus for irrigating a vas deferens having an obstruction in connection with a vasectomy reversal, the apparatus comprising:

a catheter assembly having a first end suitable for connection to a fluid reservoir and terminating at a second end in a catheter tip suitable for insertion into a vas deferens;

a vas deferens clamp having a first interactive tip and a second interactive tip where said tips interact to secure said catheter in the vas deferens during breaking up of the obstruction;

a stabilizing bar connected to said vas deferens clamp and said catheter assembly such that said vas deferens clamp and catheter assembly are held in stable position relative to each other;

a base supporting said catheter with a first end of said stabilizing bar connected to the base and a second end of the stabilizing bar connected to the vas deferens clamp; and the base comprises a closed-end forceps clamp and wherein said closed-end forceps clamp is configured to attach to tissue surrounding the vas deferens in order to hold the apparatus in close proximity to the vas deferens during breaking up of the obstruction.

\* \* \* \* \*